(12) United States Patent
Urawa

(10) Patent No.: US 7,557,217 B2
(45) Date of Patent: Jul. 7, 2009

(54) PROCESS FOR PRODUCTION OF BENZIMIDAZOLE DERIVATIVE SALT PRECIPITATE

(75) Inventor: Yoshio Urawa, Hasaki-machi (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 376 days.

(21) Appl. No.: 11/597,743

(22) PCT Filed: Jun. 29, 2005

(86) PCT No.: PCT/JP2005/011969

§ 371 (c)(1),
(2), (4) Date: Nov. 27, 2006

(87) PCT Pub. No.: WO2006/003946

PCT Pub. Date: Jan. 12, 2006

(65) Prior Publication Data

US 2007/0225502 A1    Sep. 27, 2007

(30) Foreign Application Priority Data

Jun. 30, 2004    (JP) ............................. 2004-192715

(51) Int. Cl.
 *C07D 401/12* (2006.01)
(52) U.S. Cl. .................................... 546/273.7
(58) Field of Classification Search ............... 546/273.7
See application file for complete search history.

(56) References Cited

U.S. PATENT DOCUMENTS

| 5,045,552 | A | 9/1991 | Souda et al. |
| 5,840,910 | A | 11/1998 | Souda et al. |
| 5,998,445 | A | 12/1999 | Souda et al. |

FOREIGN PATENT DOCUMENTS

| JP | 64-6270 A | 1/1989 |
| JP | 64-006270 A | 1/1989 |
| JP | 7-69888 A | 3/1995 |
| JP | 7-278141 A | 10/1995 |
| JP | 2001-039975 A | 2/2001 |
| WO | WO-01/04109 A1 | 1/2001 |
| WO | WO-03/08258 A1 | 10/2003 |
| WO | WO-03/101452 A1 | 12/2003 |

*Primary Examiner*—Patricia L Morris
(74) *Attorney, Agent, or Firm*—Birch, Stewart, Kolasch & Birch, LLP

(57) ABSTRACT

The present invention provides a process for the production of a 2-[{4-(3-methoxypropoxy)-3-methylpyridin-2-yl}methylsulfinyl]-1H-benzimidazole alkali metal salt (1), which is a drug or an intermediate for the production of a drug, the process not requiring large-scale equipment and being excellent in terms of workability, operability and energy conservation. According to the present invention, there is disclosed a process for the production of a salt precipitate represented by formula (1)

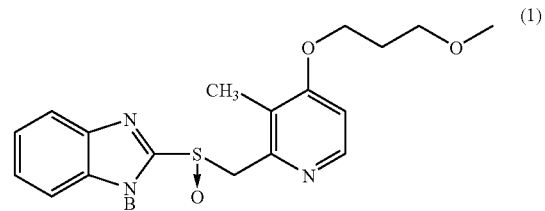

(wherein B represents an alkali metal ion), the process comprising the steps of:
 dissolving the compound represented by formula (2)

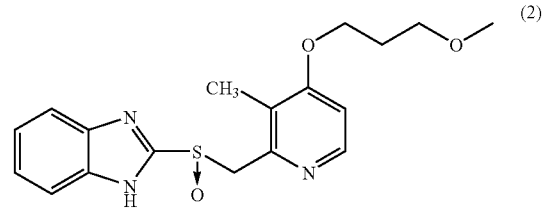

in a first organic solvent and adding an alkali metal hydroxide, or dissolving the alkali metal hydroxide in the first organic solvent and adding the compound represented by formula (2); and
 further adding a second organic solvent to a reaction mixture obtained.

6 Claims, No Drawings

PROCESS FOR PRODUCTION OF BENZIMIDAZOLE DERIVATIVE SALT PRECIPITATE

TECHNICAL FIELD

The present invention relates to a process for the production of a precipitate of a 2-[{4-(3-methoxypropoxy)-3-methylpyridin-2-yl}methylsulfinyl]-1H-benzimidazole alkali metal salt that is useful as a drug such as a gastric acid secretion inhibiting drug or an anti-ulcer drug, or an intermediate for the production of such a drug.

BACKGROUND ART

It is known that 2-[{4-(3-methoxypropoxy)-3-methylpyridin-2-yl}methylsulfinyl]-1H-benzimidazole alkali metal salts have a gastric acid secretion inhibiting action and are thus useful as anti-ulcer drugs (see Patent Document 1: U.S. Pat. No. 5,045,552). Moreover, such a salt can be produced using any of various processes, in particular a production process using a freeze drying method is known (see Patent Document 2: Japanese Patent Application Laid-Open No. H7-278141, or Patent Document 3: International Publication No. WO03/101452).

However, with the freeze drying method, large-scale equipment is required in actual production of 2-[{4-(3-methoxypropoxy)-3-methylpyridin-2-yl}methylsulfinyl]-1H-benzimidazole alkali metal salts, and moreover the method cannot necessarily be said to be excellent in terms of workability, operability and energy conservation.

DISCLOSURE OF INVENTION

Problems to be Solved by the Invention

It is thus is an object of the present invention to provide a process for the production of a 2-[{4-(3-methoxypropoxy)-3-methylpyridin-2-yl}methylsulfinyl]-1H-benzimidazole alkali metal salt that is useful as an anti-ulcer drug, the process not requiring large-scale equipment and being excellent in terms of workability, operability and energy conservation.

Means for Solving the Problems

In view of the above circumstances, the present inventor has carried out studies with vigor, and as a result have arrived at the present invention after discovering a process for the production of the salts as described above, which attains the above object, i.e. does not require large-scale equipment and is excellent in terms of workability, operability and energy conservation.

That is, the present invention provides:

[1] a process for the production of a salt precipitate represented by formula (1)

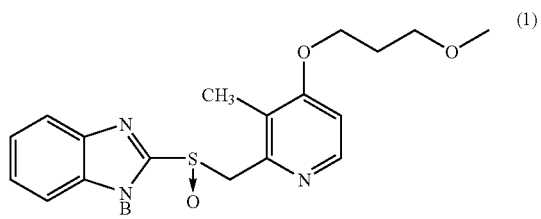

(wherein B represents an alkali metal ion), i.e. a process for the production of a 2-[{4-(3-methoxypropoxy)-3-methylpyridin-2-yl}methylsulfinyl]-1H-benzimidazole alkali metal salt (1), the process comprising the steps of:

dissolving a compound represented by formula (2)

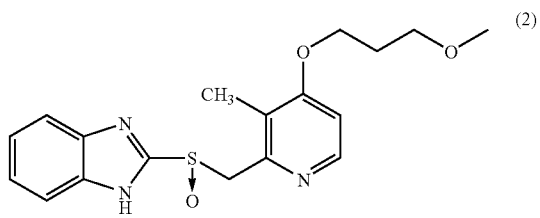

in a first organic solvent and adding an alkali metal hydroxide, or dissolving the alkali metal hydroxide in the first organic solvent and adding the compound represented by formula (2); and further adding a second organic solvent to a reaction mixture obtained, Advantageous Effects of the Invention The present invention is a useful production process, in that a 2-[{4-(3-methoxypropoxy)-3-methylpyridin-2-yl}methylsulfinyl]-1H-benzimidazole alkali metal salt (1) that is a drug or an intermediate for the production of a drug can be produced through a process that does not require large-scale equipment and is excellent in terms of workability, operability and energy conservation.

BEST MODE FOR CARRYING OUT THE INVENTION

The production process according to the present invention is a process for the production of a salt precipitate represented by formula (1)

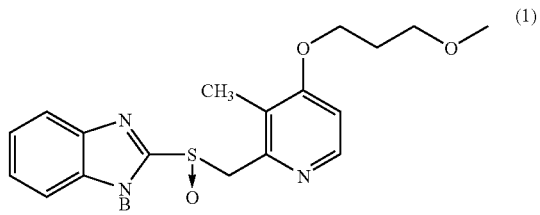

(wherein B represents an alkali metal ion), the production process comprising the steps of:

dissolving a compound represented by formula (2)

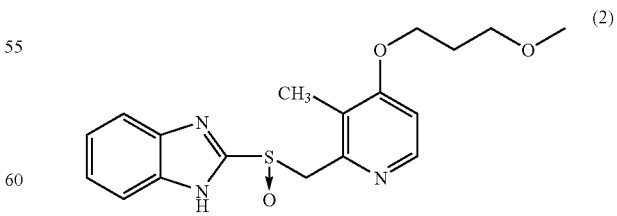

in a first organic solvent and adding an alkali metal hydroxide, or dissolving the alkali metal hydroxide in the first organic solvent and adding the compound represented by formula (2); and further adding a second organic solvent to the reaction mixture obtained.

There are no particular limitations on the first organic solvent used in the above process so long as the compound represented by formula (2) (hereinafter merely referred to as "compound (2)") dissolves therein, but an alcohol such as methanol, ethanol, propanol, isopropanol, butanol or tert-butanol are preferable, methanol or ethanol being particularly preferable.

There are no particular limitations on the second organic solvent used in the above process so long as the salt represented by formula (1) (hereinafter merely referred to as "compound (1)" or "salt (1)") does not readily dissolve therein, but an ether such as diethyl ether, diisopropyl ether, tert-butyl (methyl) ether, tetrahydrofuran, dioxane or dimethoxyethane are preferable, tert-butyl(methyl) ether or diisopropyl ether being particularly preferable.

The amount of the first organic solvent used in the above process is generally in a range of from 0.9 to 1.5 ml based on 1 g of compound (2).

The amount of the second organic solvent used in the above process is generally in a range of from 10 to 110 ml based on 1 g of compound (2).

Examples of the alkali metal hydroxide used in the above process include sodium hydroxide, potassium hydroxide or the like, sodium hydroxide being preferable.

There are no particular limitations on the amount of the alkali metal hydroxide used in the above process so long as the purity of compound (1) obtained as the precipitate is not markedly reduced, but this amount is preferably in a range of from 0.99 to 1 equivalents based on compound (2).

In the above process, there are no particular limitations on the temperature when dissolving compound (2) in the first organic solvent or in the first organic solvent in which the alkali metal hydroxide has been dissolved so long as this temperature is within a range such that decomposition of compound (2) or salt (1) does not occur, but this temperature is generally in a range of from 0 to 30° C.

In the above process, there are no particular limitations on the temperature when adding the alkali metal hydroxide to the solution of compound (2) in the first organic solvent so long as this temperature is within a range such that decomposition of compound (2) or salt (1) does not occur, but this temperature is generally in a range of from 0 to 30° C.

In the above process, the conversion from compound (2) to salt (1) generally takes place immediately.

In the above process, when adding the second organic solvent to the solution of salt (1) in the first organic solvent, it is preferable to add the second organic solvent not all at once, but rather continuously and gradually, or in divided amounts.

In the above process, the precipitate of salt (1) obtained refers to amorphous matter, crystalline matter, or a mixture thereof.

The precipitate of salt (1) obtained through the above process can be isolated by filtering off, and drying under reduced pressure or normal pressure. The isolated precipitate can be used for a desired preparation as is, or by milling it as appropriate.

The production process according to the present invention is preferably:

[2] the process according to above [1], wherein the first organic solvent is an alcohol;

[3] the process according to above [1] or [2], wherein the first organic solvent is methanol or ethanol;

[4] the process according to any one of above [1] to [3], wherein the alkali metal hydroxide is sodium hydroxide, and B is a sodium ion;

[5] the process according to any one of above [1] to [4], wherein the second organic solvent is an ether; or

[6] the process according to any one of above [1] to [5], wherein the second organic solvent is tert-butyl(methyl) ether or diisopropyl ether.

In the production process of the present invention, compound (2) used as the starting material can be produced using the process described in Patent Document 1 or a publicly known improvement of this process (e.g. Japanese Patent Application Publication No. H11-71370, Japanese Patent Application Publication No. 2000-143659, International Publication No. WO01/68594, European Patent Application Publication No. EP 1,270,555, etc.). The compound (2) can also be produced through the following process.

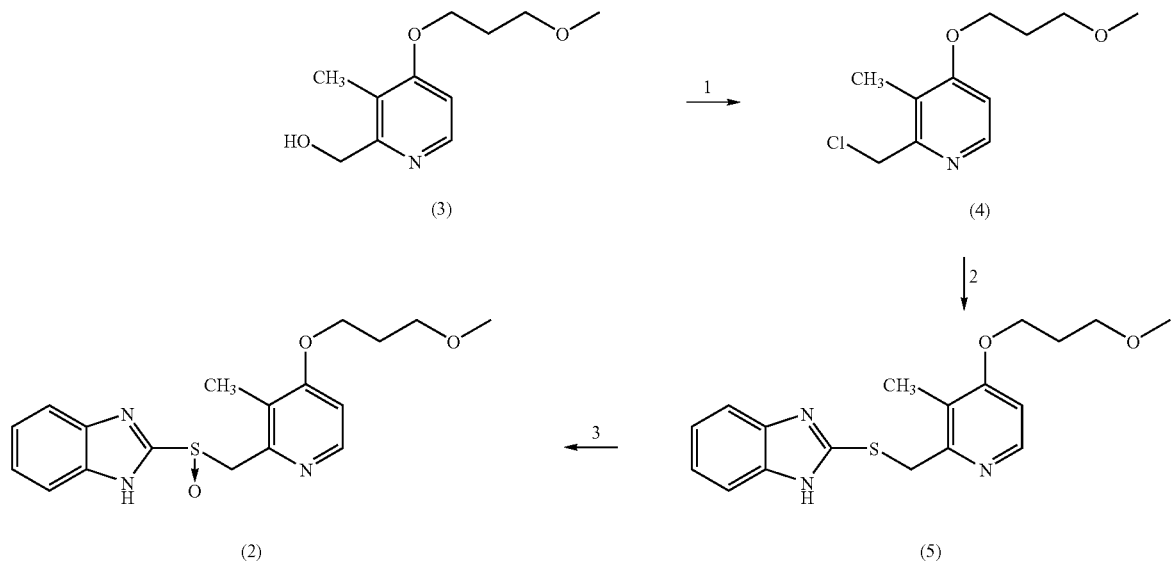

Note that the compound represented by formula (3) (hereinafter merely referred to as "compound (3)"; similar notation will also be used for the compounds represented by formulae (4) and (5)), compound (4), and compound (5) are all publicly known compounds.

First Step

This step is a step of producing compound (4) in a crude state comprising reacting compound (3) with a chlorinating agent in an inert solvent, and concentrating the reaction mixture obtained.

The present step differs from the process described in Patent Document 1 in that the reaction mixture is merely concentrated, other work up not being carried out.

There are no particular limitations on the inert solvent used in the present step so long as the starting material compound can be dissolved therein to some extent and the solvent does not impede the reaction: for example, aromatic hydrocarbons such as benzene, toluene or xylene; organic acid esters such as methyl acetate or ethyl acetate; ethers such as diethyl ether, diisopropyl ether, tetrahydrofuran, dioxane or dimethoxyethane; or halogenated hydrocarbons such as methylene chloride, chloroform, carbon tetrachloride or dichloroethane can be preferably used, toluene, ethyl acetate, dimethoxyethane or dichloromethane being particularly preferably used.

As the chlorinating agent used in the present step, for example phosphorous trichloride, phosphorus pentachloride, phosphorus oxychloride, thionyl chloride or the like can be used, but it is preferable to use one such as thionyl chloride that can be removed by being distilled off with the solvent.

The reaction temperature in the present step varies depending on the solvent, starting material compound, and chlorinating agent used and so on, but is generally in a range of from −20 to 50° C., preferably 0 to 20° C.

The reaction time in the present step varies depending on the solvent, starting material compound, chlorinating agent, and reaction temperature used and so on, but is generally in a range of from 30 minutes to 6 hours, preferably 1 to 2 hours.

After completion of the reaction, the reaction mixture is concentrated and dried under reduced pressure or normal pressure, and can then be used in the second step as is without being purified in particular.

Second Step

This step is a step of producing compound (5) by reacting compound (4) obtained in the first step with 2-benzimidazolethiol in the presence of a base in an inert solvent.

There are no particular limitations on the inert solvent used in the present step so long as the starting material compound can be dissolved therein to some extent and the solvent does not impede the reaction; for example, alcohols such as methanol, ethanol, propanol, isopropanol, butanol or tert-butanol can be used, ethanol being particularly preferably used.

There are no particular limitations on the base used in the present step so long as the base dissolves in the solvent to some extent; for example, an alkali metal hydride such as sodium hydroxide or potassium hydroxide can be used, sodium hydroxide being particularly preferably used.

The reaction temperature in the present step varies depending on the solvent, starting material compound, and base used and so on, but is generally in a range of from −20 to 70° C., preferably 20 to 60° C.

The reaction time in the present step varies depending on the solvent, starting material compound, base, and reaction temperature used and so on, but is generally in a range of from 30 minutes to 6 hours, preferably 1 to 2 hours.

After completion of the reaction, compound (5) can be isolated from the reaction mixture according to the well-known method. For example, after completion of the reaction, the reaction mixture is subjected to vacuum concentration, then extraction is carried out using water and an organic solvent immiscible with water (e.g. dichloromethane, ethyl acetate, etc.), the organic layer is washed using a sodium hydroxide aqueous solution and water, and then concentration is carried out, whereby compound (5) can be produced.

In particular, by using an organic solvent such as one of the following, highly purified compound (5) can be produced as crystals:

ethers such as diethyl ether, diisopropyl ether, tert-butyl (methyl) ether, tetrahydrofuran, dioxane or dimethoxyethane (particularly diisopropyl ether or tert-butyl(methyl) ether);

nitriles such as acetonitrile (particularly acetonitrile);

aromatic hydrocarbons such as benzene, toluene or xylene (particularly toluene);

alcohosl such as methanol, ethanol, propanol or isopropanol (particularly isopropanol);

ketones such as acetone or methyl ethyl ketone (particularly acetone);

organic acid esters such as methyl acetate, ethyl acetate, dimethyl carbonate or diethyl carbonate (particularly ethyl acetate or diethyl carbonate); or mixed solvents comprising at least two of the above solvents.

In the crystallization, the amount of the solvent used varies depending on the type of the solvent, but is in a range of from 3 to 40 ml based on 1 g of compound (5).

Third Step

This step is a step of producing compound (2) by reacting compound (5) with an oxidizing agent in an inert solvent.

There are no particular limitations on the inert solvent used in the present step so long as the starting material compound can be dissolved therein to some extent and the solvent does not impede the reaction; for example, halogenated hydrocarbons such as chloroform, dichloromethane, carbon tetrachloride or dichloroethane can be preferably used, dichloromethane being particularly preferably used.

As the oxidizing agent used in the present step, hydrogen peroxide, peracetic acid, m-chloroperbenzoic acid, sodium periodate or the like can be used, it being preferable to use m-chloroperbenzoic acid.

If one equivalent of the oxidizing agent is used based on compound (5), then compounds produced through further oxidation of compound (2) are by-produced; the oxidizing agent is thus preferably used in an amount less than one equivalent, particularly preferably in a range of from 0.3 to 0.6 equivalents.

The reaction temperature in the present step varies depending on the solvent, starting material compound, and oxidizing agent used and so on, but is generally in a range of from −50 to 0° C., preferably −30 to −10° C.

The reaction time in the present step varies depending on the solvent, starting material compound, oxidizing agent, and reaction temperature used and so on, but is generally in a range of from 30 minutes to 6 hours, preferably 1 to 2 hours.

After completion of the reaction, compound (2) can be isolated from the reaction mixture according to the well-known method. For example, the following operations are carried out in order:

operation 1: a basic aqueous solution (e.g. an aqueous solution of an alkali metal hydroxide, particularly a sodium hydroxide aqueous solution) is added to the reaction mixture obtained, the mixture is strongly stirred or shaken and then left to stand, and then the organic layer is separated off so as to obtain the aqueous layer (a);

operation 2: an organic solvent (e.g. halogenated hydrocarbons such as chloroform, dichloromethane, carbon tetrachloride or dichloroethane, particularly dichloromethane) is added to the aqueous layer (a), the mixture is strongly stirred or shaken and then left to stand, and then the organic layer is separated off so as to obtain the aqueous layer (b);

operation 3: an aqueous buffer solution (e.g. an ammonium acetate aqueous solution) and the same organic solvent as before are added to the aqueous layer (b), and with the pH in a range of from 10.0 to 10.5, the mixture is strongly stirred or shaken and then left to stand, and then separation is carried out so as to obtain the organic layer (a) and the aqueous layer (c);

operation 4: the same organic solvent as before is added to the aqueous layer (c), the mixture is strongly stirred or shaken and then left to stand, and then separation is carried out so as to obtain the organic layer (b), which is combined with the organic layer (a), and then water or aqueous sodium bicarbonate solution is added, the mixture is strongly stirred or shaken and then left to stand, and then the aqueous layer is removed and the organic layer (c) thus obtained is concentrated.

In particular, after the concentration, by carrying out crystallization using an organic solvent such as one of the following, highly purified compound (2) can be produced as crystals:

ethers such as diethyl ether, diisopropyl ether, tert-butyl (methyl) ether, tetrahydrofuran, dioxane or dimethoxyethane (particularly diethyl ether);

nitriles such as acetonitrile (particularly acetonitrile);

aromatic hydrocarbons such as benzene, toluene or xylene (particularly toluene);

alcohols such as methanol, ethanol, propanol, isopropanol or isobutanol (particularly isopropanol);

ketones such as acetone or methyl ethyl ketone (particularly acetone);

organic acid esters such as methyl acetate, ethyl acetate, dimethyl carbonate or diethyl carbonate (particularly ethyl acetate); or mixed solvents of the above solvents, particularly ethers, nitrites, ketones or organic acid esters plus halogenated hydrocarbons such as chloroform, dichloromethane, carbon tetrachloride or dichloroethane (particularly acetonitrile plus dichloromethane, acetone plus dichloromethane, ethyl acetate plus dichloromethane, or diethyl ether plus dichloromethane).

The present invention will be described in more detail below, showing Examples and Reference Examples. Note, however, that the following description is merely illustrative, the present invention not being limited thereto in any case.

The meanings of abbreviations used in the following are as follows:

mcpba: metachloroperbenzoic acid
TLC: thin layer chromatography
HPLC: high performance liquid chromatography

EXAMPLES

Example 1

2-[{4-(3-Methoxypropoxy)-3-methylpyridin-2-yl}methylsulfinyl]-1H-benzimidazole (4.97 g (13.8 mmol)) was dissolved in methanol (5 ml). Sodium hydroxide (0.559 g (13.7 mmol)) was then put into the methanol solution, and after dissolution had been confirmed, dipropyl ether (500 ml) was added slowly, whereby 2-[{4-(3-methoxypropoxy)-3-methylpyridin-2-yl}methylsulfinyl]-1H-benzimidazole sodium salt (4.77 g) was obtained through precipitation (yield 90.3%).

Example 2

Ethanol (30 ml) was added to sodium hydroxide (2.25 g (55.1 mmol)), and dissolution was carried out. 2-[{4-(3-Methoxypropoxy)-3-methylpyridin-2-yl}methylsulfinyl]-1H-benzimidazole (20.0 g (55.6 mmol)) was then put into the ethanol solution, and after dissolution had been confirmed, diisopropyl ether (2000 ml) was added slowly, whereby 2-[{4-(3-methoxypropoxy)-3-methylpyridin-2-yl}methylsulfinyl]-1H-benzimidazole sodium salt (22.8 g) was obtained through precipitation (yield 100%).

Example 3

Ethanol (22.5 ml) was added to sodium hydroxide (1.65 g (41.3 mmol)), and dissolution was carried out. 2-[{4-(3-Methoxypropoxy)-3-methylpyridin-2-yl}methylsulfinyl]-1H-benzimidazole (15.0 g (41.7 mmol)) was then put into the ethanol solution, and after dissolution had been confirmed, tert-butyl methyl ether (160 ml) was added slowly, whereby 2-[{4-(3-methoxypropoxy)-3-methylpyridin-2-yl}methylsulfinyl]-1H-benzimidazole sodium salt (15.9 g) was obtained through precipitation (yield 100%).

Reference Example 1

2-Hydroxymethyl-4-(3-methoxypropoxy)-3-methylpyridine (5.0 g (23.7 mmol)) was dissolved in toluene (40 ml), and thionyl chloride (4.23 g (35.6 mmol)) was added dropwise into the solution in a temperature that did not exceed 25° C. Stirring was carried out at room temperature, and then after it had been confirmed by TLC that the starting material had disappeared, vacuum concentration was carried out, thus obtaining 2-chloromethyl-4-(3-methoxypropoxy)-3-methylpyridine (6.13 g (yield: 97.3%)).

Reference Example 2

2-Hydroxymethyl-4-(3-methoxypropoxy)-3-methylpyridine (5.0 g (23.7 mmol)) was dissolved in ethyl acetate (40 ml), and thionyl chloride (4.23 g (35.6 mmol)) was added dropwise into the solution in a temperature that did not exceed 25° C. Stirring was carried out at room temperature, and then after it had been confirmed by TLC that the starting material had disappeared, vacuum concentration was carried out, thus obtaining 2-chloromethyl-4-(3-methoxypropoxy)-3-methylpyridine (6.14 g (yield: 97.4%)).

Reference Example 3

2-Hydroxymethyl-4-(3-methoxypropoxy)-3-methylpyridine (5.0 g (23.7 mmol)) was dissolved in dimethoxyethane (40 ml), and thionyl chloride (4.23 g (35.6 mmol)) was added dropwise into the solution in a temperature that did not exceed 25° C. Stirring was carried out at room temperature, and then after it had been confirmed by TLC that the starting material had disappeared, vacuum concentration was carried out, thus obtaining 2-chloromethyl-4-(3-methoxypropoxy)-3-methylpyridine (6.25 g (yield: 99.2%)).

Reference Example 4

2-Hydroxymethyl-4-(3-methoxypropoxy)-3-methylpyridine (5.0 g (23.7 mmol)) was dissolved in dichloromethane (40 ml), and thionyl chloride (4.23 g (35.6 mmol)) was added dropwise into the solution in a temperature that did not exceed 25° C. Stirring was carried out at room temperature, and then after it had been confirmed by TLC that the starting material had disappeared, vacuum concentration was carried out, thus obtaining 2-chloromethyl-4-(3-methoxypropoxy)-3-methylpyridine (6.23 g (yield: 99.0%)).

Reference Example 5-1

2-[{4-(3-Methoxypropoxy)-3-methylpyridin-2-yl}methylthio]-1H-benzimidazole-Producing Step 2-Chloromethyl-4-(3-methoxypropoxy)-3-methylpyridine (53.2 g (200 mmol)), denatured ethanol (320 ml), 2-benzimidazolethiol (30.2 g (201 mmol)), and sodium hydroxide (26.8 g (670 mmol)) were added together, and reaction was carried out for approximately 2 hours at 50° C. After it had been confirmed by TLC that the starting material had disappeared, vacuum concentration was carried out, and ethyl acetate (430 ml) and water (340 ml) were then added. After stirring and then leaving to stand, the aqueous layer was separated off. The organic layer was washed with a 10% sodium hydroxide aqueous solution (110 ml), and twice with water (110 ml), and then vacuum concentration was carried out, thus obtaining crude 2-[{4-(3-methoxypropoxy)-3-methylpyridin-2-yl}methylthio]-1H-benzimidazole (69.0 g) (HPLC purity 98.7%, yield 101%).

The crude 2-[{4-(3-methoxypropoxy)-3-methylpyridin-2-yl}methylthio]-1H-benzimidazole (5.00 g) was crystallized using ethyl acetate (25 ml), and then filtration was carried out, thus obtaining 2-[{4-(3-methoxypropoxy)-3-methylpyridin-2-yl}methylthio]-1H-benzimidazole (4.80 g) (HPLC purity 99.2%, yield 96.0%).

Reference Example 5-2

The crude 2-[{4-(3-methoxypropoxy)-3-methylpyridin-2-yl}methylthio]-1H-benzimidazole (5.00 g) obtained in Reference Example 5-1 was crystallized using tert-butyl(methyl) ether (30 ml), and then filtration was carried out, thus obtaining 2-[{4-(3-methoxypropoxy)-3-methylpyridin-2-yl}methylthio]-1H-benzimidazole (4.50 g) (HPLC purity 99.2%, yield 90.0%).

Reference Example 5-3

The crude 2-[{4-(3-methoxypropoxy)-3-methylpyridin-2-yl}methylthio]-1H-benzimidazole (5.00 g) obtained in Reference Example 5-1 was crystallized using diisopropyl ether (200 ml), and then filtration was carried out, thus obtaining 2-[{4-(3-methoxypropoxy)-3-methylpyridin-2-yl}methylthio]-1H-benzimidazole (4.94 g) (HPLC purity 99.1%, yield 98.8%).

Reference Example 5-4

The crude 2-[{4-(3-methoxypropoxy)-3-methylpyridin-2-yl}methylthio]-1H-benzimidazole (5.00 g) obtained in Reference Example 5-1 was crystallized using toluene (30 ml), and then filtration was carried out, thus obtaining 2-[{4-(3-methoxypropoxy)-3-methylpyridin-2-yl}methylthio]-1H-benzimidazole (4.56 g) (HPLC purity 99.1%, yield 91.2%).

Reference Example 5-5

The crude 2-[{4-(3-methoxypropoxy)-3-methylpyridin-2-yl}methylthio]-1H-benzimidazole (5.00 g) obtained in Reference Example 5-1 was crystallized using acetonitrile (40 ml), and then filtration was carried out, thus obtaining 2-[{4-(3-methoxypropoxy)-3-methylpyridin-2-yl}methylthio]-1H-benzimidazole (4.64 g) (HPLC purity 99.1%, yield 92.8%).

Reference Example 5-6

The crude 2-[{4-(3-methoxypropoxy)-3-methylpyridin-2-yl}methylthio]-1H-benzimidazole (5.00 g) obtained in Reference Example 5-1 was crystallized using isopropyl alcohol (20 ml), and then filtration was carried out, thus obtaining 2-[{4-(3-methoxypropoxy)-3-methylpyridin-2-yl}methylthio]-1H-benzimidazole (4.55 g) (HPLC purity 99.1%, yield 91.0%).

Reference Example 5-7

The crude 2-[{4-(3-methoxypropoxy)-3-methylpyridin-2-yl}methylthio]-1H-benzimidazole (5.00 g) obtained in Reference Example 5-1 was crystallized using acetone (20 ml), and then filtration was carried out, thus obtaining 2-[{4-(3-methoxypropoxy)-3-methylpyridin-2-yl}methylthio]-1H-benzimidazole (4.80 g) (HPLC purity 99.2%, yield 96.0%).

Reference Example 5-8

The crude 2-[{4-(3-methoxypropoxy)-3-methylpyridin-2-yl}methylthio]-1H-benzimidazole (5.00 g) obtained in Reference Example 5-1 was crystallized using diethyl carbonate (90 ml), and then filtration was carried out, thus obtaining 2-[{4-(3-methoxypropoxy)-3-methylpyridin-2-yl}methylthio]-1H-benzimidazole (4.85 g) (HPLC purity 99.2%, yield 97.0%).

Reference Example 6-1

2-[{4-(3-Methoxypropoxy)-3-methylpyridin-2-yl}methylthio]-1H-benzimidazole-Producing Step 2-Chloromethyl-4-(3-methoxypropoxy)-3-methylpyridine (26.6 g (100 mmol)), denatured ethanol (160 ml), 2-benzimidazolethiol (15.0 g (100 mmol)), and sodium hydroxide (13.4 g (335 mmol)) were added together, and reaction was carried out for approximately 2 hours at 50° C. After it had been confirmed by TLC that the starting material had disappeared, vacuum concentration was carried out, and toluene (300 ml) and water (168 ml) were then added. After stirring and then leaving to stand, the aqueous layer was separated off. The organic layer was washed with a 10% sodium hydroxide aqueous solution (50 ml), and twice with water (50 ml), and then vacuum concentration was carried out, thus obtaining crude 2-[{4-(3-methoxypropoxy)-3-methylpyridin-2-yl}methylthio]-1H-benzimidazole (34.8 g) (HPLC purity 98.7%, yield 101%).

Reference Example 6-2

The crude 2-[{4-(3-methoxypropoxy)-3-methylpyridin-2-yl}methylthio]-1H-benzimidazole (3.00 g) obtained in Reference Example 6-1 was crystallized using ethyl acetate (12 ml), and then filtration was carried out, thus obtaining 2-[{4-(3-methoxypropoxy)-3-methylpyridin-2-yl}methylthio]-1H-benzimidazole (2.91 g) (HPLC purity 99.3%, yield 97.0%).

Reference Example 6-3

The crude 2-[{4-(3-methoxypropoxy)-3-methylpyridin-2-yl}methylthio]-1H-benzimidazole (3.00 g) obtained in Reference Example 6-1 was crystallized using tert-butyl(methyl) ether (12 ml), and then filtration was carried out, thus obtaining 2-[{4-(3-methoxypropoxy)-3-methylpyridin-2-yl}methylthio]-1H-benzimidazole (2.79 g) (HPLC purity 99.2%, yield 93.0%).

Reference Example 6-4

The crude 2-[{4-(3-methoxypropoxy)-3-methylpyridin-2-yl}methylthio]-1H-benzimidazole (3.00 g) obtained in Reference Example 6-1 was crystallized using toluene (15 ml), and then filtration was carried out, thus obtaining 2-[{4-(3-methoxypropoxy)-3-methylpyridin-2-yl}methylthio]-1H-benzimidazole (2.84 g) (HPLC purity 99.1%, yield 94.5%).

Reference Example 6-5

The crude 2-[{4-(3-methoxypropoxy)-3-methylpyridin-2-yl}methylthio]-1H-benzimidazole (3.00 g) obtained in Reference Example 6-1 was crystallized using acetonitrile (21 ml), and then filtration was carried out, thus obtaining 2-[{4-(3-methoxypropoxy)-3-methylpyridin-2-yl}methylthio]-1H-benzimidazole (2.81 g) (HPLC purity 99.1%, yield 93.5%).

Reference Example 6-6

The crude 2-[{4-(3-methoxypropoxy)-3-methylpyridin-2-yl}methylthio]-1H-benzimidazole (3.00 g) obtained in Reference Example 6-1 was crystallized using diisopropyl alcohol (9 ml), and then filtration was carried out, thus obtaining 2-[{4-(3-methoxypropoxy)-3-methylpyridin-2-yl}methylthio]-1H-benzimidazole (2.78 g) (HPLC purity 99.4%, yield 92.5%).

Reference Example 6-7

The crude 2-[{4-(3-methoxypropoxy)-3-methylpyridin-2-yl}methylthio]-1H-benzimidazole (3.00 g) obtained in Reference Example 6-1 was crystallized using acetone (9 ml), and then filtration was carried out, thus obtaining 2-[{4-(3-methoxypropoxy)-3-methylpyridin-2-yl}methylthio]-1H-benzimidazole (2.91 g) (HPLC purity 99.3%, yield 97.0%).

Reference Example 6-8

The crude 2-[{4-(3-methoxypropoxy)-3-methylpyridin-2-yl}methylthio]-1H-benzimidazole (3.00 g) obtained in Reference Example 6-1 was crystallized using diethyl carbonate (45 ml), and then filtration was carried out, thus obtaining 2-[{4-(3-methoxypropoxy)-3-methylpyridin-2-yl}methylthio]-1H-benzimidazole (2.93 g) (HPLC purity 99.3%, yield 97.5%).

HPLC Conditions
Column: Inertsil ODS-2 (made by GL Science)
Mobile phase: acetonitrile:water:ammonium acetate=500:500:1
Flow speed: 0.7 ml/min
Column temperature: 35° C.
Detector: 258 nm Reference Example 7

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 5.37 g (21.8 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 ml), vacuum concentration was carried out, crystallization was carried out using dichloromethane (14 ml) and acetonitrile (92 ml), and then filtration was carried out, thus obtaining 2-[{4-(3-methoxypropoxy)-3-methylpyridin-2-yl}methylsulfinyl]-1H-benzimidazole (6.26 g) (HPLC purity 99.7%, yield 23.9%).

Reference Example 8

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 5.37 g (21.8 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 ml), vacuum concentration was carried out, crystallization was carried out using ethyl acetate (66 ml), and then filtration was carried out, thus obtaining 2-[{4-(3-methoxypropoxy)-3-methylpyridin-2-yl}methylsulfinyl]-1H-benzimidazole (6.15 g) (HPLC purity 99.8%, yield 23.5%).

Reference Example 9

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 7.16 g (29.1 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 ml), vacuum concentration was carried out, crystallization was carried out using dichloromethane (18 ml) and acetone (120 ml), and then filtration was carried out, thus obtaining 2-[{4-(3-methoxypropoxy)-3-methylpyridin-2-yl}methylsulfinyl]-1H-benzimidazole (8.56 g) (HPLC purity 99.7%, yield 32.7%).

Reference Example 10

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 7.16 g (29.1 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 m), vacuum concentration was carried out, crystallization was carried out using isopropyl alcohol (88 ml), and then filtration was carried out, thus obtaining 2-[{4-(3-methoxypropoxy)-3-methylpyridin-2-yl}methylsulfinyl]-1H-benzimidazole (8.29 g) (HPLC purity 99.7%, yield 31.7%).

Reference Example 11

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 7.16 g (29.1 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 ml), vacuum concentration was carried out, crystallization was carried out using acetonitrile (132 ml), and then filtration was carried out, thus obtaining 2-[{4-(3-methoxypropoxy)-3-methylpyridin-2-yl}methylsulfinyl]-1H-benzimidazole (8.25 g) (HPLC purity 99.7%, yield 31.5%).

Reference Example 12

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 8.95 g (36.4 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 ml), vacuum concentration was carried out, crystallization was carried out using acetone (165 ml), and then filtration was carried out, thus obtaining 2-[{4-(3-methoxypropoxy)-3-methylpyridin-2-yl}methylsulfinyl]-1H-benzimidazole (10.8 g) (HPLC purity 99.6%, yield 41.4%).

Reference Example 13

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 8.95 g (36.4 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into, and then extraction was carried out twice with dichloromethane (48 ml). The dichloromethane layers were washed twice with water (48 ml), vacuum concentration was carried out, crystallization was carried out using toluene (110 ml), and then filtration was carried out, thus obtaining 2-[{4-(3-methoxypropoxy)-3-methylpyridin-2-yl}methylsulfinyl]-1H-benzimidazole (10.6 g) (HPLC purity 99.6%, yield 40.4%).

Reference Example 14

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 8.95 g (36.4 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 ml), vacuum concentration was carried out, crystallization was carried out using dichloromethane (28 ml) and ethyl acetate (184 ml), and then filtration was carried out, thus obtaining 2-[{4-(3-methoxypropoxy)-3-methylpyridin-2-yl}methylsulfinyl]-1H-benzimidazole (10.9 g) (HPLC purity 99.7%, yield 41.7%).

Reference Example 15

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 10.7 g (43.7 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 ml), vacuum concentration was carried out, crystallization was carried out using acetone (198 ml), and then filtration was carried out, thus obtaining 2-[{4-(3-methoxypropoxy)-3-methylpyridin-2-yl}methylsulfinyl]-1H-benzimidazole (12.6 g) (HPLC purity 99.3%, yield 48.3%).

Reference Example 16

2-[{4-(3-Methoxypropoxy)-3-methylpyridin-2-yl}methylthio]-1H-benzimidazole (25.0 g (72.8 mmol)) was dissolved in dichloromethane, and then the solution was cooled, and mcpba (70.2% purity; 10.7 g (43.7 mmol)) was added little by little such that the internal temperature did not exceed −15° C. After the addition, a 10% sodium hydroxide aqueous solution (70.8 ml) was added, the mixture was stirred and then left to stand, and then the aqueous layer was separated off. The separated aqueous layer was washed twice with dichloromethane (48 ml). A 2N ammonium acetate aqueous solution was then put into the solution, and then extraction was carried out twice with dichloromethane (48 ml). The dichloromethane layers were washed twice with water (48 ml), vacuum concentration was carried out, crystallization was carried out using dichloromethane (27 ml) and ether (220 ml), and then filtration was carried out, thus obtaining 2-[{4-(3-methoxypropoxy)-3-methylpyridin-2-yl}methylsulfinyl]-1H-benzimidazole (14.5 g) (HPLC purity 99.1%, yield 55.4%).

HPLC Conditions
Column: Nucleosil 5c18 (made by Chemco)
Mobile phase: methanol:phosphate buffer (pH 7)=3:2
Flow speed: 1.0 ml/min
Detector: 290 nm Reference Example 17

Sodium hydroxide (0.557 g) was dissolved in ion exchange water (5 ml). 2-[{4-(3-Methoxypropoxy)-3-methylpyridin-2-yl}methylsulfinyl]-1H-benzimidazole (4.96 g) was then put into the solution, and after dissolution had been confirmed, freeze drying was carried out for 22 hours using a bottle-type freeze dryer, thus obtaining 2-[{4-(3-methoxypropoxy)-3-methylpyridin-2-yl}methylsulfinyl]1H-benzimidazole sodium salt quantitatively.

Reference Example 18

Sodium hydroxide (0.560 g) was dissolved in ion exchange water (10 ml). 2-[{4-(3-Methoxypropoxy)-3-methylpyridin-2-yl}methylsulfinyl]-1H-benzimidazole (4.98 g) was then put into solution, and after dissolution had been confirmed, freeze drying was carried out for 22 hours using a bottle-type freeze dryer, thus obtaining 2-[{4-(3-methoxypropoxy)-3-methylpyridin-2-yl}methylsulfinyl]-1H-benzimidazole sodium salt quantitatively.

Reference Example 19

Sodium hydroxide (0.507 g) was dissolved in ion exchange water (15 ml). 2-[{4-(3-Methoxypropoxy)-3-methylpyridin-2-yl}methylsulfinyl]-1H-benzimidazole (4.50 g) was then put into the solution, and after dissolution had been confirmed, freeze drying was carried out for 22 hours using a bottle-type freeze dryer, thus obtaining 2-[{4-(3-methoxypropoxy)-3-methylpyridin-2-yl}methylsulfinyl]-1H-benzimidazole sodium salt quantitatively.

Reference Example 20

Sodium hydroxide (0.506 g) was dissolved in ion exchange water (25 ml). 2-[{4-(3-Methoxypropoxy)-3-methylpyridin-2-yl}methylsulfinyl]-1H-benzimidazole (4.50 g) was then put into the solution, and after dissolution had been confirmed, freeze drying was carried out for 22 hours using a bottle-type freeze dryer, thus obtaining 2-[{4-(3-methoxypropoxy)-3-methylpyridin-2-yl}methylsulfinyl]-1H-benzimidazole sodium salt quantitatively.

Reference Example 21

Sodium hydroxide (0.556 g) was dissolved in ion exchange water (10 ml). 2-[{4-(3-Methoxypropoxy)-3-methylpyridin-2-yl}methylsulfinyl]-1H-benzimidazole (5.00 g) was then put into the solution, and after dissolution had been confirmed, the solution was put into a Tray-type freeze dryer and freeze drying was carried out, thus obtaining 2-[{4-(3-methoxypropoxy)-3-methylpyridin-2-yl}methylsulfinyl]-1H-benzimidazole sodium salt quantitatively. Here, the Tray temperature was raised to 25° C.

INDUSTRIAL APPLICABILITY

The present invention is industrial applicable, in that a 2-[{4-(3-methoxypropoxy)-3-methylpyridin-2-yl}methylsulfinyl]-1H-benzimidazole alkali metal salt (1) that is a drug or an intermediate for the production of a drug can be produced through a process that does not require large-scale equipment and that is excellent in terms of workability, operability and energy conservation.

What is claimed is:

1. A process for the production of a salt precipitate represented by formula (1)

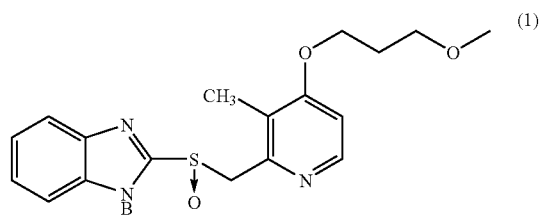

(wherein B represents an alkali metal ion), the process comprising the steps of:
dissolving a compound represented by formula (2)

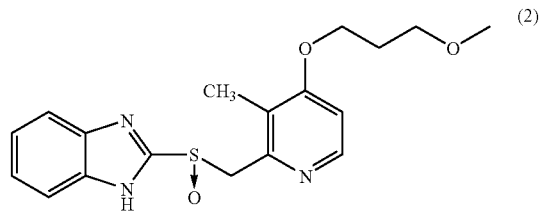

in a first organic solvent and adding an alkali metal hydroxide, or dissolving the alkali metal hydroxide in the first organic solvent and adding the compound represented by formula (2); and
further adding a second organic solvent to a reaction mixture obtained.

2. The process according to claim 1, wherein the first organic solvent is an alcohol.

3. The process according to claim 1 or 2, wherein the first organic solvent is methanol or ethanol.

4. The process according to claim 1, wherein the alkali metal hydroxide is sodium hydroxide.

5. The process according to claim 1, wherein the second organic solvent is an ether.

6. The process according to claim 1, wherein the second organic solvent is tert-butyl(methyl) ether or diisopropyl ether.

* * * * *